United States Patent [19]

McGregor et al.

[11] Patent Number: 4,792,555
[45] Date of Patent: Dec. 20, 1988

[54] PHOSPHOLIPASE $A_2$ INHIBITORS

[75] Inventors: William H. McGregor, Malvern; Joseph Y. Chang, Berwyn, both of Pa.

[73] Assignee: American Home Products Corporation, New York, N.Y.

[21] Appl. No.: 28,638

[22] Filed: Mar. 20, 1987

[51] Int. Cl.$^4$ ............... A61K 31/495; A61K 31/40; A61K 31/445; A61K 31/47; A61K 31/55; C07D 295/10; C07D 401/12; C07D 471/00

[52] U.S. Cl. ..................... 514/255; 514/212; 514/252; 514/307; 514/317; 514/323; 514/414; 514/416; 514/419; 514/423; 540/597; 540/602; 540/607; 544/360; 544/368; 544/373; 544/386; 546/146; 546/148; 546/149; 546/150; 546/152; 546/155; 546/158; 546/159; 546/192; 546/201; 546/225; 548/483; 548/496; 548/530; 548/367

[58] Field of Search ............ 540/607, 597, 602; 544/386, 360, 368, 373; 546/146, 192, 148, 149, 150, 201, 225, 152, 155, 158, 159, 192; 548/496, 483, 530, 567; 514/212, 252, 255, 307, 317, 323, 414, 416, 419, 423

[56] References Cited

U.S. PATENT DOCUMENTS 4,424,218  1/1984  Deraedt et al. ................ 514/182

OTHER PUBLICATIONS

Sole et al., Tetrahedron, vol. 42, No. p. 193–198, (1986).
Chemical Abstract, vol. 105, 97917b, (1986).
Chemical Abstract, vol. 73, 120904b, (1970).
Derwent Abstract, 23408 D/14, Continental Pharma., BE-885303, (3/19/81).
Albrecht et al., Chemical Abstract, vol. 100, 1984, 100-192284y.

Primary Examiner—Donald G. Daus
Assistant Examiner—Cecilia Shen
Attorney, Agent, or Firm—George Tarnowski

[57] ABSTRACT

There are disclosed compounds of the formula

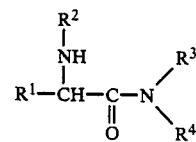

wherein $R^1$ is lower alkyl, lower alkoxycarbonyl lower alkyl, aralkoxycarbonyl, aralkoxycarbonyl lower alkyl or indol-2-yllower alkyl;

$R^2$ is hydrogen, lower alkyl or biphenylyl lower alkyl-carbonyl; or $R^1$ and $R^2$ taken together form a 5- or 6-membered saturated heterocyclic ring;

$R^3$ is hydrogen or lower alkyl;

$R^4$ is alkyl of 10–20 carbon atoms, cycloalkyl of 10–20 carbon atoms or phenylalkyl of 10–16 carbon atoms; or $R^3$ and $R^4$ taken are decahydroisoquinolin-2-yl, 3,5-dimethylpiperazin-1-yl or 3,3,5-trimethylhexahydroazepin-1-yl;

or a pharmaceutically acceptable salt thereof, and their use in the prevention and/or treatment of conditions such as allergic rhinitis, allergic bronchial asthma and other naso-bronchial obstructive air-passageway conditions, other immediate hypersensitivity reactions such as allergic conjunctivities and various inflammatory conditions.

12 Claims, No Drawings

PHOSPHOLIPASE A₂ INHIBITORS

The present invention is directed to a series of amino acid amides having anti-inflammatory activity.

It is now well-established that arachidonic acid (AA) is metabolized in mammals by two distinct pathways. The metabolism of arachidonic acid by cyclooxygenase enzymes results in the production of prostaglandins and thromboxanes. The physiological activity of the prostaglandins arise from the endoperoxides $PGG_2$ and $PGH_2$ by the cyclooxygenase pathway of arachidonic acid metabolism. These endoperoxides are also the precursors of the thromboxanes (Tx) $A_2$ and $B_2$. $TxA_2$ is a vasoconstrictor which stimulates platelet aggregation. In the normal situation, the vasoconstrictive and platelet aggregating properties of the thromboxanes are balanced by another product arising from the endoperoxides in the cyclooxygenase pathway, prostacyclin ($PGI_2$), which is a vasodilator with platelet aggregation inhibitory activity. In the event prostacyclin synthesis is impaired and/or platelet activation is enhanced, then thrombosis and vasoconstriction is favored. The role of prostanoids in haemostasis and thrombosis are reviewed by R. J. Gryglewski, *CRC Crit. Rev. Biochem.*, 7, 291 (1980) and J. B. Smith, *Am. J. Pathol.*, 99, 743 (1980).

The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $B_4$, $C_4$ and $D_4$. The substance denominated slow-reacting substance of anaphylaxis (SRS-A) has been shown to consist of a mixture of leukotrienes, with $LTC_4$ and $LTD_4$ as the primary products and having varying amounts of other leukotriene metabolites [see Bach et al., *J. Immun.* 215, 115–118 (1980); *Biochem. Biophys. Res. Commun.* 93, 1121–1126 (1980)].

The significance of these leukotrienes is that a great deal of evidence is accumulating showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., *Nature* 288, 484–486 (1980)], and another leukotriene, $LTB_4$, is a powerful chemotactic factor for leukocytes [see A. W. Ford-Hutchinson, *J. Roy. Soc. Med.*, 74, 831–833 (1981)]. The activity of leukotrienes and slow-reacting substances (SRS's) as mediators of inflammation and hypersensitivity is extensively reviewed in Bailey and Casey, *Ann. Reports Med. Chem.*, 17, 203–217 (1982).

It is now generally accepted that the release of free arachidonic acid from membrane phospholipids by the enzyme phospholipase $A_2$ ($PLA_2$) is the critical first step in the initiation of the synthesis of the various eicosanoids arising from the cyclooxygenase and lipoxygenase pathways. In this regard it may be noted that the anti-inflammatory steroids are thought to inhibit eicosanoid synthesis by inducing the synthesis of a $PLA_2$ inhibitory protein denominated macrocortin or lipomodulin [see Flower et al., *Nature, London,* 278, 456 (1979) and Hirata et al., *Proc. Natn. Acad. Sci. U.S.A.,* 77, 2533 (1980)]. $PLA_2$ catalyzes the specific hydrolysis of the fatty-acid ester linkage at the 2-position of 1,2-diacyl-sn-phosphoglycerides and two major pathways for the $PLA_2$-mediated arachidonic acid release have been proposed to account for phospholipid hydrolysis. According to the first, the $PLA_2$-mediated cleavage of AA from the 2-position of phosphatidylcholine and phosphatidylethanolamine occurs during platelet activation [Bills et al., *Biochem. Biophys. Acta,* 424, 303 (1976)], while according to the second, phosphatidylinositol, which turns over very rapidly, may also serve as the initial source of AA.

As the initial step leading to subsequent conversion of AA to the various eicosanoids by the cyclooxygenase and lipoxygenase pathways, the $PLA_2$-mediated release of AA from membrane phospholipids is a critical event in attempting to deal with the various physiological manifestations which are based on the activity of the prostaglandins, thromboxanes and leukotrienes. Thus, while $PLA_2$ has been shown to be required for platelet aggregation [Pickett et al., *Biochem. J.*, 160, 405 (1976)], cardiac contraction and excitation [Geisler et al., *Pharm. Res. Commun.*, 9, 117 (1977)], as well as prostaglandin synthesis [Vogt, *Adv. Prostagl. · Thromb. Res.*, 3, 89 (1978)], the inhibition of $PLA_2$ is indicated in the therapeutic treatment of cyclooxygenase and/or lipoxygenase pathway product-mediated physiological conditions. Thus, $PLA_2$ inhibitors are a rational approach to the prevention, removal or amelioration of such conditions as allergy, anaphylaxis, asthma and inflammation.

The invention provides novel compounds of the formula

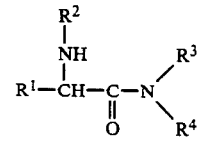

wherein $R^1$ is lower alkyl, lower alkoxycarbonyl lower alkyl, aralkoxycarbonyl, aralkoxycarbonyl lower alkyl or indol-2-yllower alkyl;

$R^2$ is hydrogen, lower alkyl or biphenylyl lower alkylcarbonyl; or $R^1$ and $R^2$ taken together form a 5- or 6-membered saturated heterocyclic ring;

$R^3$ is hydrogen or lower alkyl;

$R^4$ is alkyl of 10-20 carbon atoms, cycloalkyl of 10-20 carbon atoms or phenylalkyl of 10-16 carbon atoms; or $R^3$ and $R^4$ taken together are decahydroisoquinolin-2-yl, 3,5-dimethylpiperazin-1-yl or 3,3,5-trimethylhexahydroazepin-1-yl;

or a pharmaceutically acceptable salt thereof.

The terms "lower alkyl" and "lower alkoxy," when used alone or in combination, refer to moieties having 1–6 carbon atoms in the carbon chain. The term "aralkoxy" refers to moieties having 7–10 carbon atoms.

The compounds of the invention can be prepared by the following reaction scheme

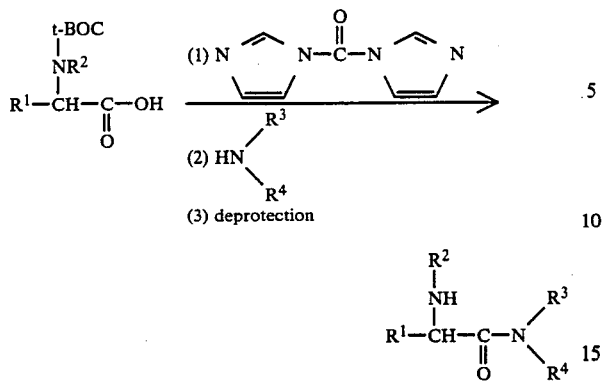

wherein the protected amino acid starting material is initially reacted with carbonyl diimidazole in an organic solvent, preferably dried tetrahydrofuran followed by reaction of the intermediate so formed with the amine reactant $HNR^3R^4$ to form the protected form of the desired final product. The final step in the preparation scheme involves deprotection of the protected final product amino acid amide by conventional means. A preferred method involves deprotection with hydrogen chloride in organic solvent, such as for example ethyl acetate.

The starting materials used in the preparation of the compounds of the invention are commercially available or can be prepared by conventional procedures taught in the chemical literature. Thus, starting amino acids such as norleucine, proline, homoproline and tryptophan are commercially available, and benzyl-$\beta$-aspartate, N-biphenylylacetylnorleucine and N-phenylheptanylnorleucine can be readily prepared by conventional preparative methods from the constituent amino acids and the appropriate carboxy or amino group substituents. The t-BOC protected amino acid starting materials are also readily prepared by well-established amino group protection techniques. In like manner, the starting $HNR^3R^4$ compounds, such as 2,6-dimethylpiperazine and 3,3,5-trimethylhexahydroazepine are commercially available and starting compounds such as decahydroisoquinoline and the various alkyl-, cycloalkyl- and phenylalkyl-amines are either commercially available or can be prepared by known preparative schemes conventional in the chemical arts.

The compounds of the invention are capable of forming pharmaceutically acceptable salts, including the salts of pharmaceutically acceptable organic and inorganic acids such as hydrochloric, hydrobromic, sulfuric, nitric, phosphoric, methanesulfonic, benzenesulfonic, acetic, citric, fumaric, maleic, malic, succinic and the like.

The compounds of the invention, by virtue of their ability to inhibit activity of $PLA_2$ enzyme, are useful in the treatment of conditions mediated by products of the oxidation of arachidonic acid. Accordingly, the compounds are indicated in the prevention and treatment of such conditions as allergic rhinitis, allergic bronchial asthma and other naso-bronchial obstructive air-passageway conditions, other immediate hypersensitivity reactions, such as allergic conjunctivitis; and various inflammatory conditions such as those present in rheumatoid arthritis, osteoarthritis, tendinitis, bursitis, psoriasis (and related skin inflammation) and the like.

When the compounds of the invention are employed in the treatment of allergic airways disorders or in anti-inflammatory therapy, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol. The compounds may also be used topically and for this purpose they may be formulated in the form of dusting powders, creams or lotions in pharmaceutically acceptable vehicles, which are applied to affected portions of the skin.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The standard pharmacological procedures, which are described fully in the examples given hereafter, illustrate the ability of the compounds of the invention to inhibit the activity of $PLA_2$ enzyme in vitro; measure the in vivo activity of the compounds as anti-inflammatory agents in the murine ear edema and paw edema assays; and measure the ability of the compounds to inhibit the synthesis of arachidonic acid, $PGE_2$ and $LTC_4$.

EXAMPLE 1

2-Amino-N-hexadecylhexanamide, hydrochloride 3 meq. (0.69 g) of t-BOC-norleucine and 3 meq. (0.49 g) of carbonyl diimidazole are combined in 15 ml of molecular sieve-dried tetrahydrofuran and reacted for 1.5 hours at ambient temperature. To this reaction mixture are added 3 meq. (0.72 g) 1-hexadecylamine in tetrahydrofuran at 0° C. over a period of 10–20 minutes, and reacted overnight at ambient temperature. The tetrahydrofuran is then removed under reduced pressure and the residue dried in vacuo.

The protected product so obtained is purified by silica gel chromatography (2×100 cm column, 3.5 ml fractions) in a 10:1 methylene chloride:methanol solvent system and the purified product is dried in vacuo at ambient temperature.

Deprotection of the purified t-BOC-protected product is accomplished by treatment of the protected product with 20 ml of 5N hydrochloric acid in ethyl acetate for 1.5 hours at ambient temperature. After reaction, ethyl ether is added and the solvent mixture is removed in vacuo. This procedure is repeated several times. The resulting product is collected by triturating with ethyl ether, filtering, washing with ether on the filter and drying in vacuo at ambient temperature to yield 550 mg of title product having a melting point of 108°–110° C.

Analysis for: $C_{22}H_{46}N_2O$: Calculated: C, 67.60; H, 12.04; N, 7.17. Found: C, 67.13; H, 12.05; N, 7.27.

IR: KBr 1460, 1480, 1650, 2840, 2910.

NMR: 0.95(t,6H-$CH_3$), 1.30(s, 36H-$CH_2$), 3.3(m, 1H-CHNH$_2$-), 3.8(m, 1H-$CH_2$-NH), 8.35(s, 1H-CONH).

EXAMPLE 2

Following the procedure of Example 1, using t-BOC-norleucine and cyclododecylamine, 3,3,5-trimethylhexahydroazepine and decahydroisoquinoline, respectively, there are prepared the following:

(a) 2-Amino-N-cyclododecylhexanamide, hydrochloride.

Yield: 390 mg; melting point 209°–14° C.

Analysis for: $C_{18}H_{36}N_2O$: Calculated: C, 64.96; H, 11.13; N, 8.42. Found: C, 65.16; H, 11.19; N, 8.68.

IR: KBr 1465, 1545, 1680, 2850, 2930.

NMR: 0.88 (t, 3H-$CH_3$); 1.40 (s, 28H-$CH_2$); 4.3 (m, H-CH-$NH_2$); 8.3 (s, 1H, C-O-NH).

(b) 1-[(S)-2-Amino-1-oxohexyl]hexahydro-3,3,5-trimethyl-1H-azepine, hydrochloride.

Yield: 140 mg

Analysis for: $C_{15}H_{30}N_2O$: Calculated: C, 61.94; H, 10.74; N, 9.63. Found: C, 61.80; H, 10.52; N, 9.35.

IR: KBr 1375, 1455, 1640, 2940.

NMR: 0.9 (m, 12H-$CH_3$); 1.4 (m, 10H-$CH_2$); 3.0 (m, 1H, CH-$NH_2$); 3.5 (m, 4H-$CH_2$-N).

(c) 2-[(S)-2-Amino-1-oxohexyl]decahydroisoquinoline, hydrochloride hemihydrate.

Yield: 200 mg

Analysis for: $C_{15}H_{28}N_2O$: Calculated: C, 60.48; H, 10.15; N, 9.41. Found: C, 61.13; H, 10.11; N, 9.41.

IR: KBr 1450, 1635, 2840, 2900.

NMR: 0.9 (m, 3H-$CH_3$); 1.4 (m, 16H, $CH_2$); 3.2 (m, 1H-CH-$NH_2$); 3.9 (m, 2H, $CH_2$-N).

EXAMPLE 3

N-[(S)-1-Butyl-2-(3,5-dimethyl-1-piperazinyl)-2-oxoethyl]benzeneheptanamide

This compound is prepared following the procedure of Example 1. However, the starting amino acid component is first prepared by reacting the methyl ester of norleucine with 7-phenylheptanoic acid to yield N-phenylheptanoylnorleucine methyl ester. The latter is saponified to yield the free acid, which is then reacted with 2,6-dimethylpiperazine according to the procedure of Example 1, with the omission of the deprotection step. This procedure yields 563 mg of title compound.

Analysis for: $C_{25}H_{41}N_3O_2$: Calculated: C, 72.25; H, 9.94; N, 10.11. Found: C, 71.15; H, 9.78; N, 9.96.

EXAMPLE 4

N-[1-[(3,5-Dimethyl-1-piperazinyl)carbonyl]pentyl][1,1'-biphenyl]-4-acetamide

Following the procedure of Example 3, and using 4-biphenylacetic acid, norleucine methyl ester and 2,6-dimethylpiperazine, there is obtained the title compound in 375 mg yield.

Analysis for: $C_{26}H_{35}N_3O_2$: Calculated: C, 74.07; H, 8.37; N, 9.97. Found: C, 73.04; H, 8.43; N, 9.85.

EXAMPLE 5

Following the procedure of Example 1, and using t-BOC-proline or t-BOC-homoproline and 1-hexadecylamine, cyclododecylamine, decahydroisoquinoline or 4-phenylbutylamine, there are prepared the following compounds:

(a) N-(S)-Hexadecyl-2-pyrrolidinecarboxamide.

Yield: 420 mg and melting point of 95°–97° C.

Analysis for: $C_{21}H_{42}N_2O$: Calculated: C, 67.25; H, 11.50; N, 7.47. Found: C, 66.39; H, 11.32; N, 7.58.

IR: KBr 1460, 1560, 1670, 2850, 2920.

NMR: 0.88 (t, 3H-$CH_3$); 1.30 (s, 32H-$CH_2$); 8.65 (s, 1H-CONH); 4.75 (m, 1H, CH-NH).

(b) N-(R)-Hexadecyl-2-pyrrolidinecarboxamide.

Yield: 450 mg and melting point of 62°–63° C. uncorr.

Analysis for: $C_{21}H_{42}N_2O$: Calculated: C, 67.25; H, 11.50; N, 7.47. Found: C, 66.73; H, 11.59; N, 7.61.

NMR: 0.90 (t, $CH_3$); 1.30 (s, $CH_2$); 4.75 (CH-NH); 8.6 (CO-NH).

(c) N-Cyclododecyl-2-pyrrolidinecarboxamide, hydrochloride.

Yield: 300 mg and melting point of 162°–164° C.

Analysis for: $C_{17}H_{32}N_2O$: Calculated: C, 64.45; H, 10.43; N, 8.85. Found: C, 64.15; H, 10.40; N, 8.89.

IR: KBr 1470, 1550, 1685, 2770, 2870, 2940, 3270.

NMR: 1.34 (s, 26H-$CH_2$); 3.5 (m, 1H, CH-NH); 4.0 (m, 2H-$CH_2$-NH); 8.4 (d, 1H-CO-NH).

(d) N-Cyclododecyl-2-piperidinecarboxamide, hydrochloride.

Yield: 380 mg and melting point of 247°–249° C. dec.

Analysis for: $C_{18}H_{34}N_2O$: Calculated: C, 65.33; H, 10.66; N, 8.47. Found: C, 65.08; H, 10.56; N, 8.64.

IR: KBr 1440, 1470, 1565, 1680, 2930, 3220.

NMR: 1.41 (s, 25H-$CH_2$); 3.4 (m, 1H, CH-NH); 3.8 (m, 2H-$CH_2$-NH).

(e) N-(4-Phenylbutyl)-2-piperidinecarboxamide, hydrochloride.

Yield: 250 mg and melting point of 140°–142° C.

Analysis for: $C_{16}H_{24}N_2O$: Calculated: C, 64.74; H, 8.49; N, 9.44. Found: C, 64.34; H, 8.44; N, 9.28.

IR: KBr 1435, 1492, 1565, 1670, 2930, 3210.

NMR: 1.8 (m, 14H-$CH_2$); 3.3 (m, 1H, CH-NH); 7.2 (m, 5H-phenyl); 8.6 (d-1H-CONH).

(f) Decahydro-2-(2-piperidininylcarbonyl)isoquinoline, hydrochloride.

Yield: 220 mg and melting point of 256°–257° C.

Analysis for: $C_{15}H_{26}N_2O$: Calculated: C, 62.81; H, 9.49; N, 9.77. Found: C, 61.81; H, 9.31; N, 9.46.

IR: KBr cm$^{-1}$ 900, 1250, 1395, 1435, 1635, 2690, 2900.

NMR: 1.5 (m, 18H, $CH_2$); 3.2 (m, 1H-CHNH); 4.4 (m, 12H, $CH_2NH$).

EXAMPLE 6

(S)-α-Amino-N-cyclododecyl-1H-indole-3-propanamide, hydrochloride

Following the procedure of Example 1 and using t-BOC-tryptophan and cyclododecylamine, there is prepared the title compound in 550 mg yield with a melting point of 164°–166° C.

Analysis for: $C_{23}H_{35}N_3O$: Calculated: C, 68.04; H, 8.94; N, 10.35. Found: C, 67.88; H, 8.91; N, 10.38.

IR: KBr 735, 1335, 1465, 1655, 2920.
NMR: 1.3 (bs, 24H-CH$_2$); 3.3 (t, 1H, CH-NH$_2$); 3.9 (1H, CH-NH); 7.2 (m, 4H-indole).

EXAMPLE 7

(S)-3-Amino-4-(cyclododecylamino)-4-oxobutanoic acid phenylmethyl ester, hydrochloride Following the procedure of Example 1 and using t-BOC-benzyl-β-aspartate and cyclododecylamine, there is prepared the title compound in 350 mg yield with a melting point of 75°–79° C.

Analysis for: C$_{23}$H$_{36}$N$_2$O$_3$: Calculated: C, 65.00; H, 8.78; N, 6.59. Found: C, 65.20; H, 8.95; N, 6.49.

IR: KBr 1463, 1540, 1670, 1720, 2920.
NMR: 1.30 (bs, H, CH$_2$); 3.2 (m, 1H, CH-NH$_2$); 7.3 (m, 5H-phenyl); 8.5 (bs, 1H-CO-NH).

EXAMPLE 8

The ability of the compounds to inhibit the activity of PLA$_2$ enzyme is measured in the following in vitro assay.

The assay is carried out as follows:

Substrate Preparation

E. coli, cultured to exponential growth, are sedimented for 15 minutes at 10,000 g and resuspended in sterile isotonic saline (1–3 ml). 10–25 μCi [1-$^{14}$C] oleic acid (or arachidonic acid) is added to a sterile flask, evaporated by N$_2$ and resolubilized with 0.3 ml 20% fatty acid-free BSA. 75–100 ml of nutrient broth and 1 ml E. coli are then added to each flask and incubated for 2–3 hours at 37° C. [1-$^{14}$C] oleic acid labelled E. coli are then sedimented, suspended in saline and added to fresh nutrient broth and incubated for 1.5 hours at 37° C. to complete [1-$^{14}$C] oleic acid incorporation into the phospholipids. After overnight refrigeration of cultures, E. coli are again sedimented, suspended in saline and autoclaved for 15 minutes at 120° C. E. coli cultures are washed twice with saline (first wash contains 1% BSA) and resuspended in saline. Non-labelled E. coli cultures are also prepared in the same manner. Cell number is determined by measuring the optical density at 550 nm (3×10 cell/ml=1 O.D.). The amount of radioactivity associated with cells is determined by counting a defined volume of cell suspension. The specific activity is subsequently adjusted by adding non-labelled E. coli to yield 2–4×10 cpm per 1×10$^{10}$ E. coli [1-$^{14}$C] Arachidonic acid-labelled E. coli are similarly prepared.

Platelet PLA$_2$ Preparation

Expired human platelets from the blood bank are centrifuged for 15 minutes at 200 g to obtain a platelet rich plasma fraction and to remove the red blood cells. Platelets are sedimented for 15 minutes at 2500 g and the plasma is removed before adding cold 0.18N H SO$_4$ (4 ml/unit). Platelets are homogenized, incubated for 1 hour at 4° C., homogenized again and centrifuged for 15 minutes at 10,000 g. The PLA$_2$ enriched supernatant fluid is removed and the amount of protein is determined by the Lowry method. The preparation is divided into various portions and stored at −20° C.

Assay of PLA$_2$ Activity

The assay measures the hydrolysis of E. coli membrane phospholipids and the release of free [1-$^{14}$C] oleic acid from the C-2 position of phospholipids by human platelet PLA$_2$. To ice cold 15×100 mm test tubes, the following additions are made: 2,5×10 E. coli (equivalent to 4 nmol phospholipid), 5 mM Ca$^{++}$, 100 mM Tris buffer (pH=7.4), 100 μg platelet extract (or an amount to produce 20–30% hydrolysis), drug or vehicle. The final volume is adjusted to 500 μl with water. Mixtures are vortexed and incubated for 30 minutes in a shaking water bath. It should be noted that preliminary experiments are always performed with each new batch of platelets to establish linear hydrolysis of phospholipids with regard to protein concentration and time. The enzyme reaction is stopped by the addition of 3 volumes of chloroform to each tube which is vortexed and then centrifuged for 5 minutes at 500 g. The lower chloroform/methanol phase is removed and evaporated under N. The dried residue is redissolved in 50 μl CHCl$_3$:CH$_3$OH (9:1 v/v), spotted on aluminum-backed chromatographic plates and developed in a solvent system consisting of petroleum ether:diethyl ether:acetic acid (80:20:1). Free fatty acid ([1-$^{14}$C]oleic acid) and [1-$^{14}$C]oleic acid labeled phospholipids are visualized with exposure to iodine vapors. Radioactive areas that cochromatographed with authentic oleic acid and phospholipid standards are cut out and placed in a scintillation vial. One ml CH$_3$OH and 10 ml Hydrofluor are added to each cut strip and radioactivity is determined by liquid scintillation counting.

The percent hydrolysis is calculated by the following equation:

$$\% \text{ Hydrolysis} = \frac{\text{free fatty acid (dpm)}}{\text{total phospholipid + free fatty acid (dpm)}}$$

Rate of Hydrolysis (nmol/min) =

$$\frac{\% \text{ hydrolysis} \times \text{total phospholipid content (5 nmol)}}{\text{incubation time (min)}}$$

| Drug | Inhibition of PLA$_2$ Activity IC$_{50}$, μM |
|---|---|
| Indomethacin | 48 |
| Gold Sodium Thiomalate | 43 |

When tested in the above-described assay, the compounds of the invention gave the following results:

TABLE 1

| Compound of Example No. | % Inhibition of PLA$_2$ (at 100 μM) |
|---|---|
| 1 | 99 |
| 2a | 76 |
| 2b | 25 |
| 2c | 24 |
| 3 | 64 |
| 4 | 52 |
| 5a | 92 |
| 5b | 98 |
| 5c | 58 |
| 5d | 45 |
| 5f | 24 |
| 6 | 52 |
| 7 | 60 |

The results show the compounds of the invention to have PLA$_2$ inhibitory activity in the assay in question.

EXAMPLE 9

The ability of the compounds of the invention to inhibit PLA$_2$ is further examined in the in vivo 12-O-tetradecanoylphorbol acetate (TPA)-induced murine ear edema test.

According to this test, Swiss Webster female mice (Buckshire), approximately 8 weeks old, are placed into plastic boxes in groups of six. Eight groups of mice receive TPA topically on the right ear. TPA is dissolved in acetone at a concentration of 100 µg/ml. The phlogistics are applied to the right ear by the means of an automatic pipet. Volumes of 10 µl are applied to the inner and outer surfaces of the ear. Each mouse receives 4 µg/ear TPA. The left ear (control) receives acetone delivered in the same manner. Oral dosing with test compound is done 30 minutes after treatment with TPA.

Measurements are taken with Oditest calipers, 0-10 mm with 0.01 graduations. The right and left ears are measured 4 hours after TPA-induced inflammation.

The difference between right and left ear thickness is calculated and the significance is determined by a one way analysis of variance with Dunnett's comparisons to control (P=0.05). Drug effects are expressed as a percent change from control values:

$$\% \text{ change from control} = \frac{(\text{Rt. ear} - \text{Lt. ear})\text{drug} - (\text{Rt. ear} - \text{Lt. ear})\text{control}}{(\text{Rt. ear} - \text{Lt. ear})\text{control}} \times 100$$

The results for the compounds of the invention are presented in Table 2.

TABLE 2

| Mouse Ear Edema Assay | |
|---|---|
| Compound of Example No. | % Change from Control (mg/kg) |
| 1 | −25 |
| 2a | −60 |
| 3 | −39 |
| 5a | −53 |

The results show that the compounds of the invention tested demonstrate oral activity against TPA-induced mouse ear edema, evidencing an inhibitory effect on acute skin inflammation mediated by products of the lipoxygenase and/or cyclooxygenase pathway.

EXAMPLE 10

The compounds of the invention are further tested in the rat carrageenan paw edema assay to determine their ability to inhibit the acute inflammatory response.

This assay is carried out as follows:

140-180 gm male Sprague-Dawley rats, in groups of 6 animals are injected subcutaneously in the right paw with 0.1 ml of 1% carrageenan at zero time. Mercury plethysmographic readings (ml) of the paw are made at zero time and 3 hours later. Test compounds are suspended or dissolved in 0.5% methylcellulose and given perorally 1 hour prior to carrageenan administration.

The increase in paw volume (edema in ml.) produced by the carrageenan is measured. Paw edema is calculated (3 hour volume minus zero time volume), and percent inhibition of edema is determined. Unpaired Student's t-test used to determine statistical significance.

The activity of standard drugs in this assay is as follows:

| Drug | Oral ED$_{50}$(95% C.L.)mg/kg |
|---|---|
| Indomethacin | 3.7 (0.6, 23.8) |

-continued

| Drug | Oral ED$_{50}$(95% C.L.)mg/kg |
|---|---|
| Aspirin | 145.4 (33.1, 645.6) |
| Phenylbutazone | 26.2 (2.3, 291.0) |

When tested in this assay, the compounds of the invention gave the following results:

TABLE 3

| Compound of Example No. | % Inhibition at 100 mg/kg (peroral) |
|---|---|
| 2a | 22 |
| 5a | 26 |
| 5b | 26 |

The results show that the compounds tested have activity in the rat carrageenan paw edema assay, evidencing an effect on the acute inflammatory response.

EXAMPLE 11

The ability of the compounds of the invention to inhibit both leukotriene and prostaglandin synthesis is examined in an assay which measures the ability of the compounds of the invention to inhibit the synthesis of arachidonic acid, PGE$_2$ and LTC$_4$ by murine peritoneal macrophages.

The assay is carried out as follows:

Macrophages are removed from the peritoneal cavity of 55-57 day old CD-1 mice (killed by CO$_2$ asphyxiation) by peritoneal lavage and centrifuged at 400×g for ten minutes. The cells are resuspended in Medium 199 and $4 \times 10^6$ cells are allowed to adhere on $35 \times 10$ mm Petri dishes for 1.5 hours at 37° C. in an atmosphere of 95% air and 5% CO$_2$. The cell monolayers are washed and incubated overnight in Medium 199 supplemented with 10% heat inactivated bovine serum containing 1µCi[$^{14}$C]-arachidonic acid, or in the absence of $^{14}$C-arachidonic acid when the supernatant is to be assayed by radioimmunoassay (RIA). The labeled cells are then washed and incubated at 37° C. for 2 hours in Medium 199 with the prostaglandin stimuli, zymosan, or 12-o-tetradecanoyl-phorbol-13-acetate (TPA) and in the presence or absence of test compounds. Following incubation, the supernatant is removed and subjected to radioimmunoassay in order to determine the percent inhibition of arachidonic acid, prostaglandin E$_2$ and leukotriene C$_4$ by the test compounds. The results in the assay for compounds of the invention, expressed as IC$_{50}$ values, are presented in Table 4.

TABLE 4

| Compound of Example No. | IC$_{50}$ (µM) | | |
|---|---|---|---|
| | AA | PGE$_2$ | LTC$_4$ |
| 5a | 19.6 | 13.7 | 7.6 |

The results show that the compound tested has a significant inhibitory effect on the synthesis of AA, PGE$_2$ and LTC$_4$ by murine peritoneal macrophages, evidencing an inhibitory effect on PLA$_2$.

We claim:

1. A compound having the formula

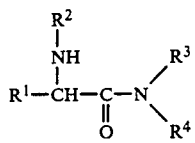

wherein
- $R^1$ is lower alkyl, lower alkoxycarbonyl lower alkyl, phenyl $C_{1-3}$ alkoxycarbonyl, aralkoxycarbonyl lower alkyl or indol-2-yllower alkyl;
- $R^2$ is hydrogen, lower alkyl or biphenylyl lower alkylcarbonyl; or
- $R^1$ and $R^2$ taken together form a pyrrolidine or piperidine ring;
- $R^3$ is hydrogen or lower alkyl;
- $R^4$ is alkyl of 10–20 carbon atoms, cycloalkyl of 10–20 carbon atoms or phenylalkyl of 10–16 carbon atoms; or
- $R^3$ and $R^4$ taken together are decahydroisoquinolin-2-yl, 3,5-dimethylpiperazin-1-yl or 3,3,5-trimethylhexahydroazepin-1-yl, with the provisos that (i) at least one of the pair, $R^1$ and $R^2$ or $R^3$ and $R^4$ must be taken together to form a heterocyclic ring as hereinbefore defined and (ii) that when $R^1$ and $R^2$ taken together form a pyrrolidine ring, $R^4$ is other than alkyl of 10–20 carbon atoms;

or a pharmaceutically acceptable salt thereof.

2. The compound of claim 1, having the name 1-[(S)-2-amino-1-oxohexyl]hexahydro-3,3,5-trimethyl-1H-azepine.

3. The compound of claim 1, having the name 2-[(S)-2-amino-1-oxohexyl]decahydroisoquinoline.

4. The compound of claim 1, having the name N-[(S)-1-butyl-2-(3,5-dimethyl-1-piperazinyl)-2-oxoethyl]benzeneheptanamide.

5. The compound of claim 1, having the name N-[1-[(3,5-dimethyl-1-piperazinyl)carbonyl]pentyl]-[1,1'-biphenyl]-4-acetamide.

6. The compound of claim 1, having the name N-cyclododecyl-2-pyrrolidinecarboxamide.

7. The compound of claim 1, having the name N-cyclododecyl-2-piperidinecarboxamide.

8. The compound of claim 1, having the name N-(4-phenylbutyl)-2-piperidinecarboxamide.

9. The compound of claim 1, having the name decahydro-2-(2-piperidinylcarbonyl)isoquinoline.

10. The compound of claim 1, having the name (S)-α-amino-N-cyclododecyl-1H-indole-3-propanamide.

11. A method for treating inflammatory conditions which comprises administering to a subject in need thereof an anti-inflammatory effective amount of a compound having the formula

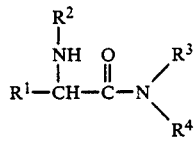

wherein
- $R^1$ is lower alkyl, lower alkoxycarbonyl lower alkyl, phenyl $C_{1-3}$ alkoxycarbonyl, aralkoxycarbonyl lower alkyl or indol-2-yllower alkyl;
- $R^2$ is hydrogen, lower alkyl or biphenylyl lower alkylcarbonyl; or
- $R^1$ and $R^2$ taken together form a pyrrolidine or piperidine ring;
- $R^3$ is hydrogen or lower alkyl;
- $R^4$ is alkyl of 10–20 carbons atoms, cycloalkyl of 10–20 carbon atoms or phenylalkyl of 10–16 carbon atoms; or
- $R^3$ and $R^4$ taken together are decahydroisoquinolin-2-yl, 3,5-dimethylpiperazin-1-yl or 3,3,5-trimethylhexadroazepin-1-yl, with the proviso that at least one of the pair $R^1$ and $R^2$ or $R^3$ and $R^4$ must be taken together to form a heterocyclic ring as hereinbefore defined;

or a pharmaceutically acceptable salt thereof.

12. A pharmaceutical composition for treating inflammatory conditions comprising a compound having the formula

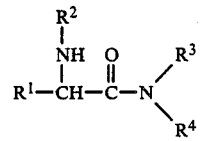

wherein
- $R^1$ is lower alkyl, lower alkoxycarbonyl lower alkyl, phenyl $C_{1-3}$ alkoxycarbonyl, aralkoxycarbonyl lower alkyl or indol-2-yllower alkyl;
- $R^2$ is hydrogen, lower alkyl or biphenylyl lower alkylcarbonyl; or
- $R^1$ and $R^2$ taken together form a pyrrolidine or piperidine ring;
- $R^3$ is hydrogen or lower alkyl;
- $R^4$ is alkyl of 10–20 carbon atoms, cycloalkyl of 10–20 carbon atoms or phenylalkyl of 10–16 carbon atoms; or
- $R^3$ and $R^4$ taken together are decahydroisoquinolin-2-yl, 3,5-dimethylpiperazin-1-yl or 3,3,5-trimethylhexahydroazepin-1-yl, with the proviso that at least one of the pair $R^1$ and $R^2$ or $R^3$ and $R^4$ must be taken together to form a heterocyclic ring as hereinbefore defined;

and a pharmaceutically acceptable carrier.

* * * * *